(12) United States Patent
Diers

(10) Patent No.: US 8,371,309 B2
(45) Date of Patent: Feb. 12, 2013

(54) INTRAORAL APPARATUS FOR TREATING UPPER AIRWAY DISORDERS

(76) Inventor: Neslon R. Diers, Cincinnati, OH (US)

(*) Notice: Subject to any disclaimer, the term of this patent is extended or adjusted under 35 U.S.C. 154(b) by 447 days.

(21) Appl. No.: 12/732,490

(22) Filed: Mar. 26, 2010

(65) Prior Publication Data

US 2011/0232651 A1   Sep. 29, 2011

(51) Int. Cl.
*A61F 5/56* (2006.01)
(52) U.S. Cl. ........................................................ 128/848
(58) Field of Classification Search .................. 128/848, 128/859–862; 602/902; 433/6, 7
See application file for complete search history.

(56) References Cited

U.S. PATENT DOCUMENTS

| | | | | |
|---|---|---|---|---|
| 4,637,796 A | * | 1/1987 | Korn | 433/7 |
| 4,752,222 A | * | 6/1988 | Bass | 433/7 |
| 4,798,534 A | * | 1/1989 | Breads | 433/6 |
| 4,901,737 A | * | 2/1990 | Toone | 128/848 |
| 4,976,614 A | * | 12/1990 | Tepper | 433/18 |
| 5,092,346 A | | 3/1992 | Hays et al. | |
| 5,277,202 A | | 1/1994 | Hays et al. | |
| 5,368,477 A | * | 11/1994 | Neeley | 433/6 |
| 5,752,822 A | | 5/1998 | Robson | |
| 5,865,619 A | * | 2/1999 | Cross et al. | 433/6 |
| 6,418,933 B1 | | 7/2002 | Strong | |
| 7,328,705 B2 | | 2/2008 | Abramson | |
| 7,581,542 B2 | | 9/2009 | Abramson | |
| 2004/0013993 A1 | * | 1/2004 | Ito | 433/6 |
| 2006/0078840 A1 | | 4/2006 | Robson | |
| 2007/0224567 A1 | | 9/2007 | Robson | |

* cited by examiner

*Primary Examiner* — Patricia Bianco
*Assistant Examiner* — Raymond E Harris
(74) *Attorney, Agent, or Firm* — Ronald J. Richter; Hasse & Nesbitt LLC

(57) ABSTRACT

A removable intraoral apparatus for improving airway patency is described. Wearing the apparatus alters the position, configuration and freedom of movement of the tongue, the muscles of mastication, as well as the pharyngeal and facial muscles. The apparatus is useful for correcting snoring and/or obstructive sleep apnea due to intermittent closures or partial obstructions occurring in the oropharynx during sleep. The apparatus of the invention can improve various types of airway disorders and improve oral functions by changing the position, configuration and freedom of movement of selected portions of the tongue and mouth, reducing the resistance to air flow in the mouth and pharynx, re-orienting and reprogramming the muscles of the mouth and tongue, and maintaining a proper oral systemic balance.

15 Claims, 5 Drawing Sheets

INTRAORAL APPARATUS FOR TREATING UPPER AIRWAY DISORDERS

FIELD OF THE INVENTION

This invention relates to the field of oral appliances and dental orthotics. In particular, the present invention relates to a wearable intraoral apparatus for relieving upper airway disorders including snoring, obstructive sleep apnea and related problems.

BACKGROUND OF THE INVENTION

Upper airway disorders in patients can result in a variety of difficulties, such as obstructive sleep apnea, snoring, labored breathing, oxygen starvation, and the resulting physical impairments arising from such disorders including headaches, chronic fatigue, sleep problems, and problems chewing, swallowing and speaking. The pathogenesis of airway obstruction that characterizes upper airway disorders can include both anatomic and functional abnormalities of the upper airway that result in increased air flow resistance. Such abnormalities may include narrowing of the upper airway due to suction forces created during inspiration, the effect of gravity pulling the tongue back to oppose the pharyngeal wall, and insufficient muscle tone in the upper airway dilator muscles, among others. It is also believed that excessive soft tissue in the anterior and lateral neck, as commonly observed in obese persons, can apply sufficient pressure to internal structures to narrow the upper airway and restrict air flow.

The tongue is normally maintained in a somewhat forward position under autonomic nervous control, which in turn is effected by the medulla of the brain. This autonomic control may not be maintained in a person who is sleeping, semi-conscious, unconscious or under heavy sedation. When one's head is oriented with the mouth pointing upwards, should the tongue become too relaxed it can fall back towards the throat, reducing the flow of air in to the lungs or even closing the airway. If a severe closure condition is not corrected within several minutes, this can reduce oxygen saturation in the brain, and, if left uncorrected, can lead to irreversible brain damage or even death. In order for the tongue to be able to stay forward, it is important for the tension on the major muscle of the tongue (the genioglossus muscle) and the pharyngeal muscles to be maintained.

Oral appliances are sometimes used in order to open the airway behind the tongue and allow easier breathing through the nose and mouth. For example, U.S. Pat. No. 5,752,822 to Robson discloses a mandibular appliance which has tongue positioning extensions designed to elevate the tongue and move it forward to reduce or relieve symptoms related to upper airway disorders. While useful, this device acts upon the tongue only and does not address other portions of the mouth and airway. U.S. Pat. No. 7,328,705 to Abramson discloses an anti-snoring device comprising the combination of an intraoral nasal dilator and a mandibular repositioner. This device fits over the mandibular teeth and is bulky. U.S. Pat. No. 5,794,627 to Frantz et al. discloses an orthotic that extends an elastic band between top and bottom trays and pulls the jaw forward to reduce sleep apnea and snoring. Again, this is a bulky device and can also cause the mandible to be pulled forward with a relatively constant force, causing unwanted discomfort of the jaw muscles.

Function regulating devices, such as "Frankel" and "bionator" devices, have been used to treat juvenile malocclusion such as overbite or overjet by gradually adjusting the bite over time. These devices are generally used on children whose jaws are in the process of developing and can be more easily adjusted. This usually corresponds with children ages 8-12, and the devices are typically worn for 12-24 hours at a time. For example, the Function Regulator II (FR-II) was developed by Professor Rolf Frankel of Germany to produce changes in jaw relationships in persons with Class II malocclusion. The Frankel function regulator is a one-piece, removable appliance designed to promote proper dental arch development and jaw relationship during childhood/adolescence. The appliance is intended to work within the vestibule of the mouth and hold away the tissue of the cheeks, lips and chin, allowing the skeletal system to develop in its most natural way.

While such prior art devices may be useful for their intended purposes, they can be quite uncomfortable to wear, causing muscle strain, pain and/or discomfort in the jaw, neck and tongue. Thus, there remains a need for an improved apparatus that is both comfortable to wear and useful for maintaining a patent airway during sleep. It would also be beneficial to provide an intraoral apparatus for treating and correcting upper airway disorders and related problems such as snoring, muscle contraction problems, neck and head pain, obstructive sleep apnea, and other conditions. It would also be beneficial to provide an intraoral device that re-orients and reprograms the muscles of the tongue and mouth in order to establish a new postural performance pattern for the muscles of the face, mouth and neck, so that a more beneficial physiological function of the upper airway can be obtained. There is also a need for a wearable intraoral apparatus that has high patient acceptance and comfort while relieving upper airway disorders and related problems, leading to better treatment success.

SUMMARY OF THE INVENTION

In light of the foregoing, the present invention provides a removable intraoral apparatus for treating and correcting upper airway disorders. The apparatus of the invention can change the position, configuration and freedom of movement of selected portions of the tongue and mouth, reduce the resistance to air flow in the mouth and pharynx, re-orient and reprogram the muscles of the mouth and tongue, and maintain a proper oral systemic balance.

A first aspect of the invention provides a removable intraoral apparatus for relieving upper airway disorders, the apparatus comprising, in combination: supports comprising: a pair of lingual shields for engaging the inferior portion of the tongue and advancing the mandible; a palatal wafer for engaging the hard palate and controlling the tongue position; a pair of lip pads for engaging the mental-labial fold; and a pair of buccal shields for engaging the interior surfaces of the cheeks; and reinforcement members anchored in the supports for interconnecting and reinforcing the supports, wherein wearing of the apparatus alters the position, configuration and freedom of movement of the tongue, the muscles of mastication, and the pharyngeal and facial muscles to reduce airflow resistance and alleviate upper airway disorders.

A second aspect of the invention provides an apparatus for relieving upper airway disorders, comprising, in combination: a pair of lingual shields for engaging the tongue and advancing the mandible of a user; a palatal wafer for engaging the hard palate and controlling the anterior tongue position; a pair of lip pads for engaging the mental-labial fold; a pair of buccal shields for engaging the interior surfaces of the cheeks and pushing the cheeks laterally; and a pair of upper molar stop wires for creating a physical barrier to closing the upper and lower teeth together and preventing the appliance from rocking in the superior inferior direction when in use, wherein each upper molar stop wire projects from the posterior portion of a corresponding buccal shield, wherein the lingual shields, palatal wafer, lip pads and buccal shields are connected to one another and reinforced by one or more reinforcement members, and wherein the apparatus alters the position, configuration and freedom of movement of the tongue, the muscles of mastication, and the pharyngeal and facial muscles to reduce resistance of air flow in the mouth and pharynx.

A third aspect of the invention provides a method for re-orienting and reprogramming the muscles of the tongue and mouth in order to cause a decreased resistance to airflow in the mouth and pharynx, the method comprising the steps of: providing supports for engaging the soft tissues of the mouth, the supports comprising a pair of lingual shields, a palatal wafer, a pair of lip pads, and a pair of buccal shields, wherein the lingual shields, palatal wafer, lip pads and buccal shields are connected to one another and reinforced by one or more reinforcement members; and arranging the supports and reinforcement members in the mouth of a user so that the lingual shields engage the inferior portion of the tongue and advance the mandible, the palatal wafer engages the hard palate and controls the anterior tongue position, the lip pads engage the mental-labial fold, and the buccal shields engage the interior surfaces of the cheeks, wherein the supports and reinforcement members, used in combination, help the user achieve a reduced resistance to air flow in the mouth and pharynx and allows for better physiological function in breathing, speaking, chewing, and swallowing.

The nature and advantages of the present invention will be more fully appreciated from the following drawings, detailed description and claims.

BRIEF DESCRIPTION OF THE DRAWINGS

A more complete appreciation of the present invention and many of the principles and attendant advantages thereof will be readily understood by reference to the following detailed description when taken in conjunction with the accompanying drawings, in which.

DETAILED DESCRIPTION OF THE INVENTION

The present invention teaches a novel tissue-borne apparatus (i.e. having minimal contact with the teeth, as opposed to a tooth-borne appliance) for improving airway patency. Wearing the apparatus alters the position, configuration and freedom of movement of the tongue, the muscles of mastication, as well as the pharyngeal and facial muscles. The apparatus is useful for correcting snoring and/or obstructive sleep apnea due to intermittent closures or partial obstructions occurring in the hypopharynx and oropharynx during sleep. The apparatus generally functions to open the airway by repositioning the mandible in a more inferior and anterior position, causing the jaw to be more open and to protrude more, as compared to the normal closed position of the jaw. Since the apparatus is tissue-borne, it typically rests in the user's mouth without engaging or moving the teeth, but rather seeks stabilization and retention in the various grooves or troughs of the oral cavity. The apparatus typically employs a heat-curable plastic, such as dental acrylic or methyl methacrylate, for making relatively rigid yet flexible support sections or plates. These plates are interconnected by one or more reinforcement members or dental wires for stabilization of the appliance.

Figure 1:
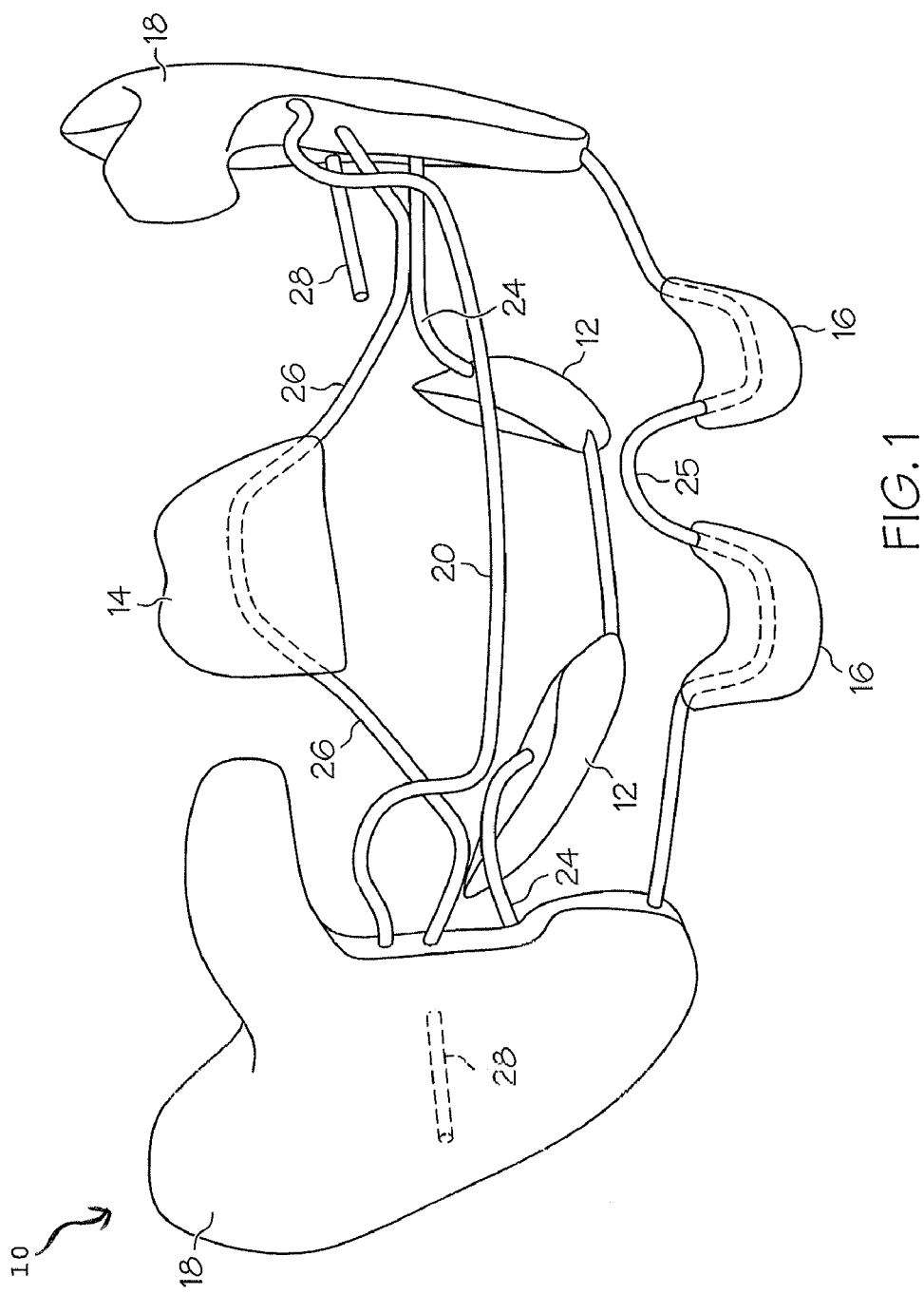
FIG. 1 is a front perspective view of one embodiment of the apparatus of the present invention.

FIG. 1-FIG. 3 and FIG. 5 represent various views of one embodiment of the apparatus of the invention. As illustrated in FIG. 1, the apparatus 10 generally includes a pair of lingual shields 12, a palatal wafer 14, a pair of lip pads 16 and a pair of buccal shields 18. Reinforcement members or wires 20, 22, 24 and 26 are typically incorporated or bonded within these supports by embedding them in a liquid orthodontic acrylic that forms the supports. Thus the wires are bonded within the supports 12-18 to interconnect them, and the supports are also thereby joined to one another, adding stability and rigidity to the appliance and allowing the various supports and wiring to function together as a single unit.

Figure 2:
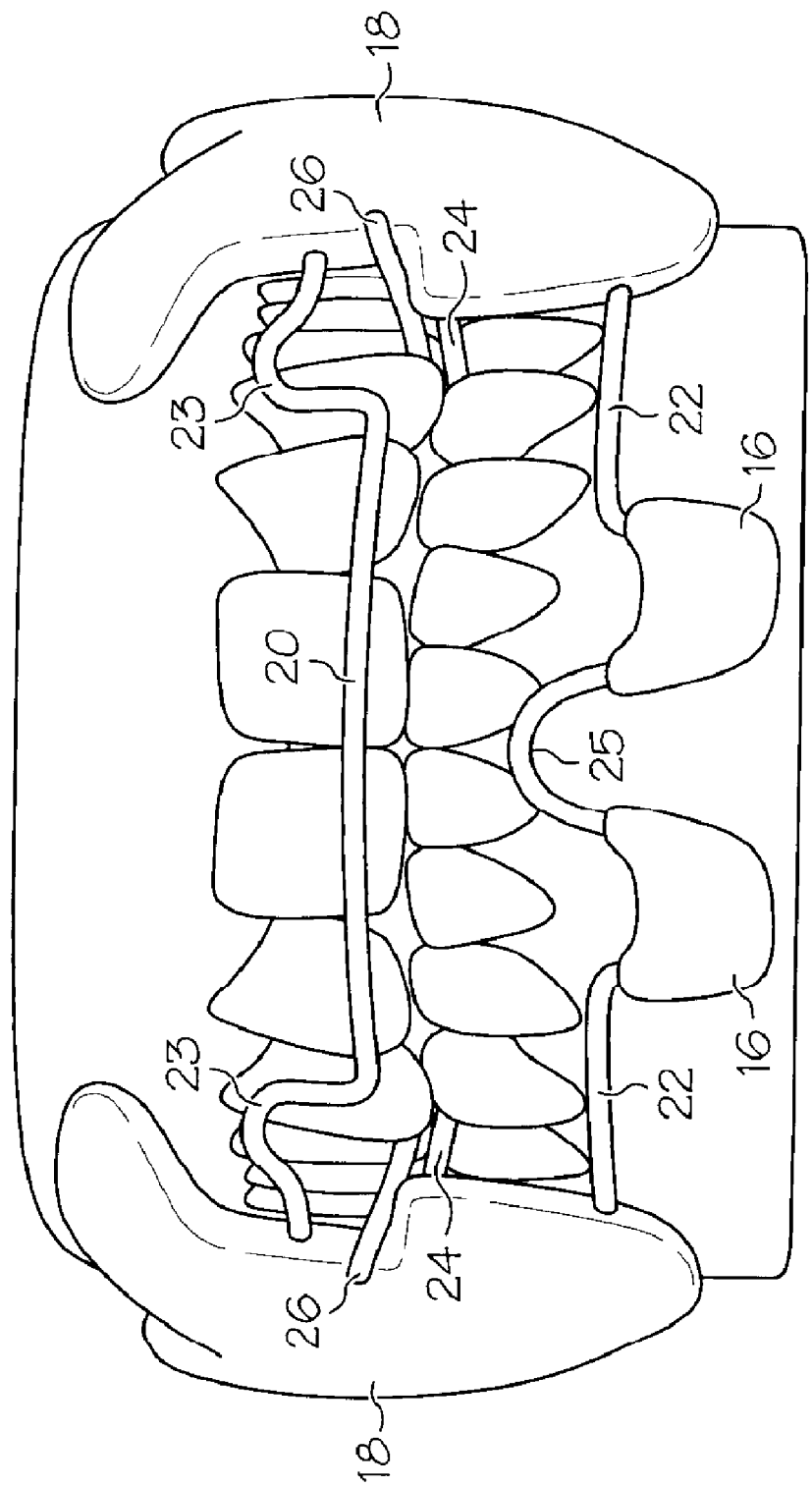
FIG. 2 is a front perspective view of the apparatus of FIG. 1 when inserted into a user's mouth.
Figure 3:
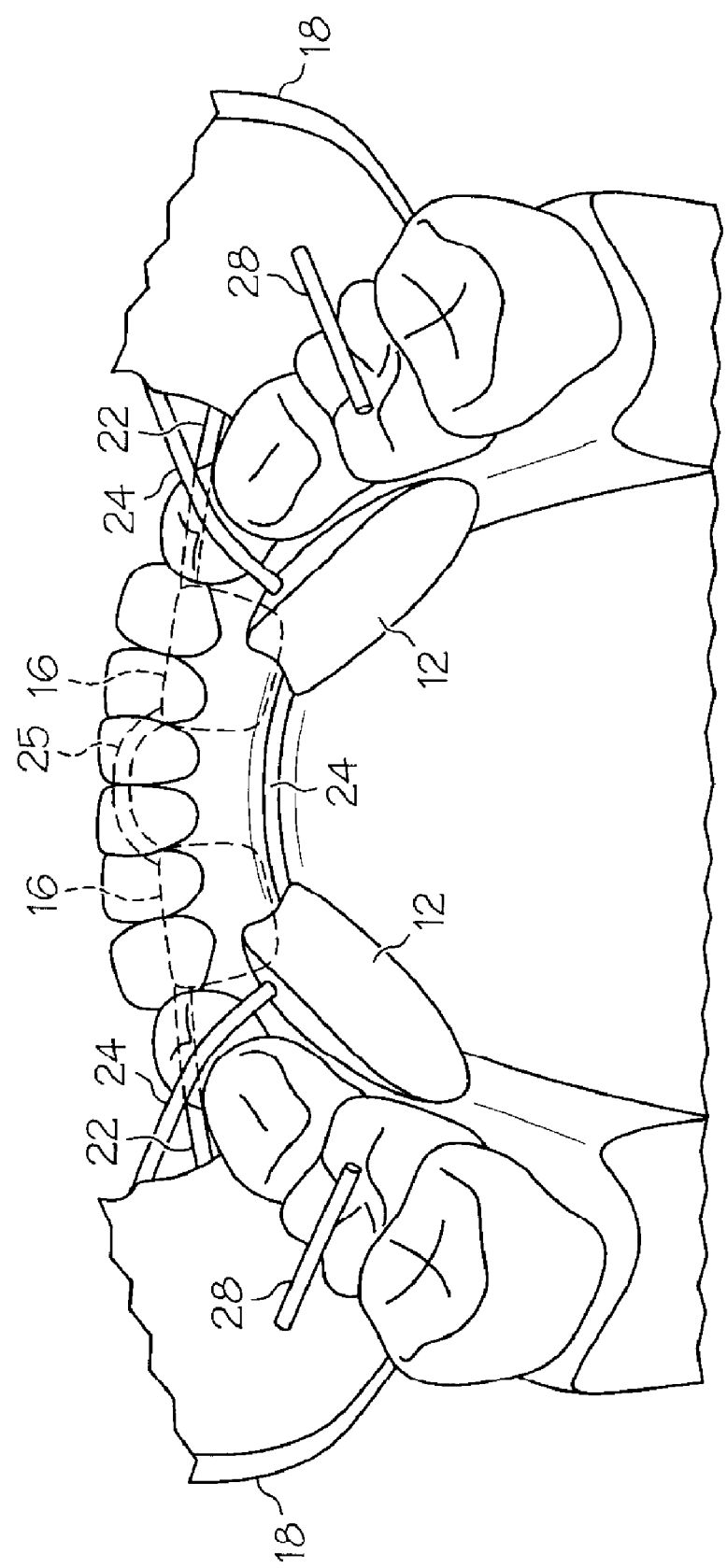
FIG. 3 is a top sectional view of the apparatus of FIG. 1 relative to the mandibular (lower) dental arch of a user.

As illustrated in FIG. 1, a labial wire 20 is designed to anteriorly connect and support the buccal shields 18. The clinician can adjust vertical loops 23 of the labial wire 20 on either side of the cuspids, as best seen in FIG. 2, allowing the buccal shields 18 to be expanded or contracted in a lateral direction to alter the position of the buccal shields and, when expanded, allow the buccal shields to further open the vestibule of the mouth. Mental wires 22 also anteriorly connect the buccal shields 18 and further serve to support the lip pads 16 between the buccal shields 18. A small vertical loop wire 25 is located between the mental wires 22 that can be expanded or contracted in order to alter the position of the lip pads 16 anteriorly or posteriorly, for comfort. Lingual shield cross-over wires 24, as best seen in FIG. 3, support the lingual shields 12 between the buccal shields 18 and adds lateral rigidity to the appliance. Palatal wires 26 connect the buccal shields 18 to the palatal wafer 14.

Figure 5:
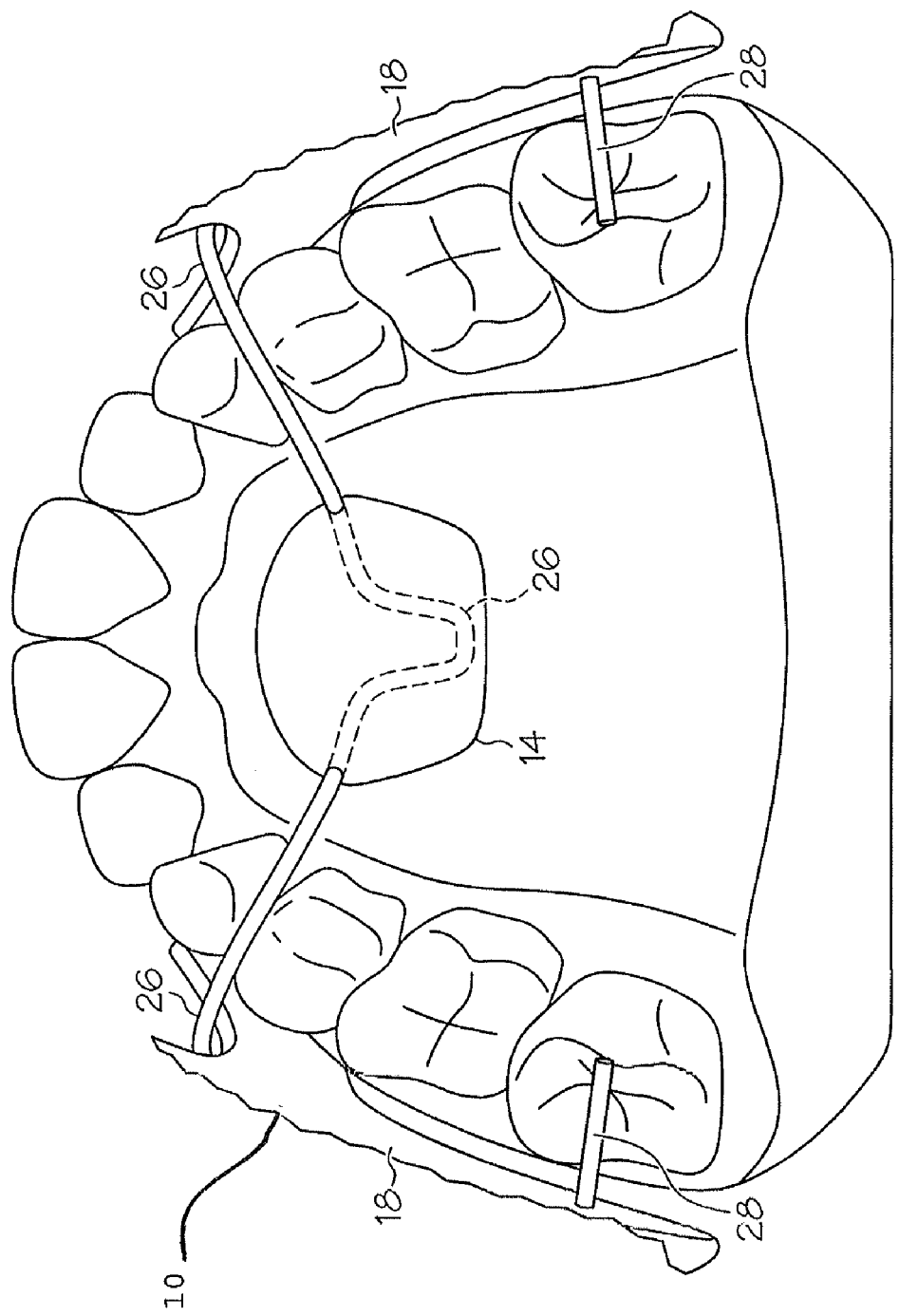
FIG. 5 is a bottom sectional view of the apparatus of FIG. 1 relative to the maxillary (upper) dental arch of a user.

Upper molar stop wires 28 can be best seen in FIG. 5, and are a pair of wires that project from the posterior portion of each of the buccal shields 18. The upper molar stop wires 28 are typically seated on the user's upper molar teeth and act to cause a physical barrier to closing the upper and lower teeth together. This increases the vertical distance of the oral cavity, thereby improving airway patency and allowing more room for the tongue to move. The molar stop wires 28 also prevent the appliance 10 from rocking in the superior inferior (posterior) direction and works in conjunction with the palatal wafer 14, which acts as an anterior stop by contacting the hard palate. If needed, lower posterior molar stop wires (not shown) can also be integrated to project from the posterior portion of each of the lingual shields 12 of the device, and can work synergistically with the upper molar stop wires to add to the physical barrier to closing the teeth, and further increase the vertical distance of the oral cavity.

The tongue pads or lingual shields 12 are preferably seated under the tongue on either side of a user's mouth adjacent the mandibular second bicuspid and first molar. See FIGS. 1 and 3. The lingual shields 12 typically engage the inferior portion (or underside) of the tongue, so that the user's tongue is elevated and moved forward to an upward and anterior position as it rests upon the upper surface of the shields. This also causes the mandible to advance forward. By doing so, an appropriate volume of the tongue is positioned in the oral cavity above the lingual shields to relieve upper airway restrictions behind the oral cavity. The lingual shields 12 generally function to "tighten" and re-train the muscles of mastication, specifically the lateral pterygoid, geniohyoid, mylohyoid, and digrastric muscles to accept a new postural position. More specifically, the lingual shields 12 press on the lingual inferior alveolar tissues and activate the inferior head of the lateral pterygoid muscle, the geniohyoid and mylohyoid muscles, and the anterior belly of the digastric muscle to reflexly posture the tongue forward. The lingual shields 12 thus act to advance the tongue forward, causing pain unless the lateral pterygoid muscle also reflexly pushes the mandible, or lower jaw, forward. Therefore, the lingual shields cause the wearer to automatically reposition the mandible in a more anterior (protrusive) position as compared to the normal closed position of the jaw. The lingual shields 12 typically have a convex contour at a central region. More specifically, the inner posterior and anterior surfaces of the lingual shields engaged by the tongue are typically concave and the edges of the lingual shields are rounded, which allows the tongue to move comfortably to the upper surface of the lingual shields. To further facilitate the comfort of the user, the upper surfaces of the lingual shields engaged by the tongue are polished. Furthermore, the lingual shields are typically contoured to ensure that they do not impinge on the lateral surface of the tongue. When positioned beneath the tongue, the lingual shields 12 provide a slide for the tongue so that it can easily elevate and come forward in the mouth. This serves to establish a new working posture for the lower jaw and tongue through proprioceptive feedback.

In use, the user's tongue rests on an upper surface of the lingual shields 12. The lingual shields are configured such that the depth of the lingual shields are sufficient at a posterior portion to prevent the tongue from moving below the lingual shields, but is sufficiently small to prevent the lingual shields from impinging on the tissues of the floor of the user's mouth and the tissues of the tongue base, or from inhibiting forward motion of the tongue. Their shape allows for repositioning of the jaw forward via proprioceptive feedback, such as by positioning the jaw forward in order to prevent pain. In this manner, the lingual shields allow for tongue movement, and the user is able to swallow without impingement or discomfort. Although the depth of the lingual shields may vary from user to user, a typical depth usually falls within the range of 8-10 mm superiorly. The thickness of the shields is about 2-3 mm, and the length of each shield averages about 30 mm.

As noted above the lingual shields 12 are typically connected to one another by crossover wiring 24, and each shield is also connected by this crossover wiring 24 to its corresponding buccal shield 18 on that side of the mouth. The wiring connecting one lingual shield to the other, besides adding rigidity to the appliance, allows the mandibular lingual frenum (i.e. the vertical band of oral mucosa connecting the tongue with the floor of the oral cavity and the alveolar ridge) of the user to function without interference. The bow shape of the crossover wiring 24 between the lingual shields 12 also allows for easy adjustment of the lingual shields.

As seen in FIG. 5, the palatal wafer 14 engages and seats itself on the surface of the hard palate of the maxilla. This causes the anterior tip of the tongue to reflexly posture down, while the posterior portion of the tongue comes forward and up. The palatal wafer 14 acts generally to bring the hyoid bone in the neck forward, and accomplishes this by causing the geniohyoid muscle to contract and the genioglossus muscle (the major muscle of the tongue) to retract The hyoid bone, which supports the muscles of the throat and the voice box, is pulled upward. The palatal wafer 14 is also able to provide palatal stimulation, causing the anterior tip of the tongue to turn down and forward and thus bring the entire posterior surface of the tongue anteriorly, away from the posterior pharynx. This activation of the superior and inferior hyoid muscles causes a repositioning of the hyoid bone in a more superior-anterior position.

The wafer 14 is sloped so as to fill in any crevices and voids which will not allow the tongue to maintain intimate contact with the hard palate. The wafer, on the side touching the palate, intimately touches the anterior palatal ridge. The wafer, on the tongue side, is so designed to allow the tongue to maintain continuous contact when swallowing, talking, chewing and breathing. It eliminates voids in the palate where the tongue could not easily posture forward. The wafer 14 functions to re-establish anatomically correct palatal contours so that the tongue can assume a more forward and upward position in the mouth. The palatal wafer 14 thus functions to re-contour the palate, allowing for the engagement of, and continuous contact with, the middle and anterior portions of the tongue, similarly to a suckling process for a baby with a pacifier, thereby bringing the posterior portion of the tongue away from the posterior pharynx and opening the airway. Yet another of the functions of the palatal wires 26 and the palatal wafer 14 is to cooperate with the buccal shields 18 to position, or center, the appliance relative to the maxillary arch. The palatal wires 26 also support the position of the palatal wafer 14 in relation to the buccal shields 18.

Figure 4:
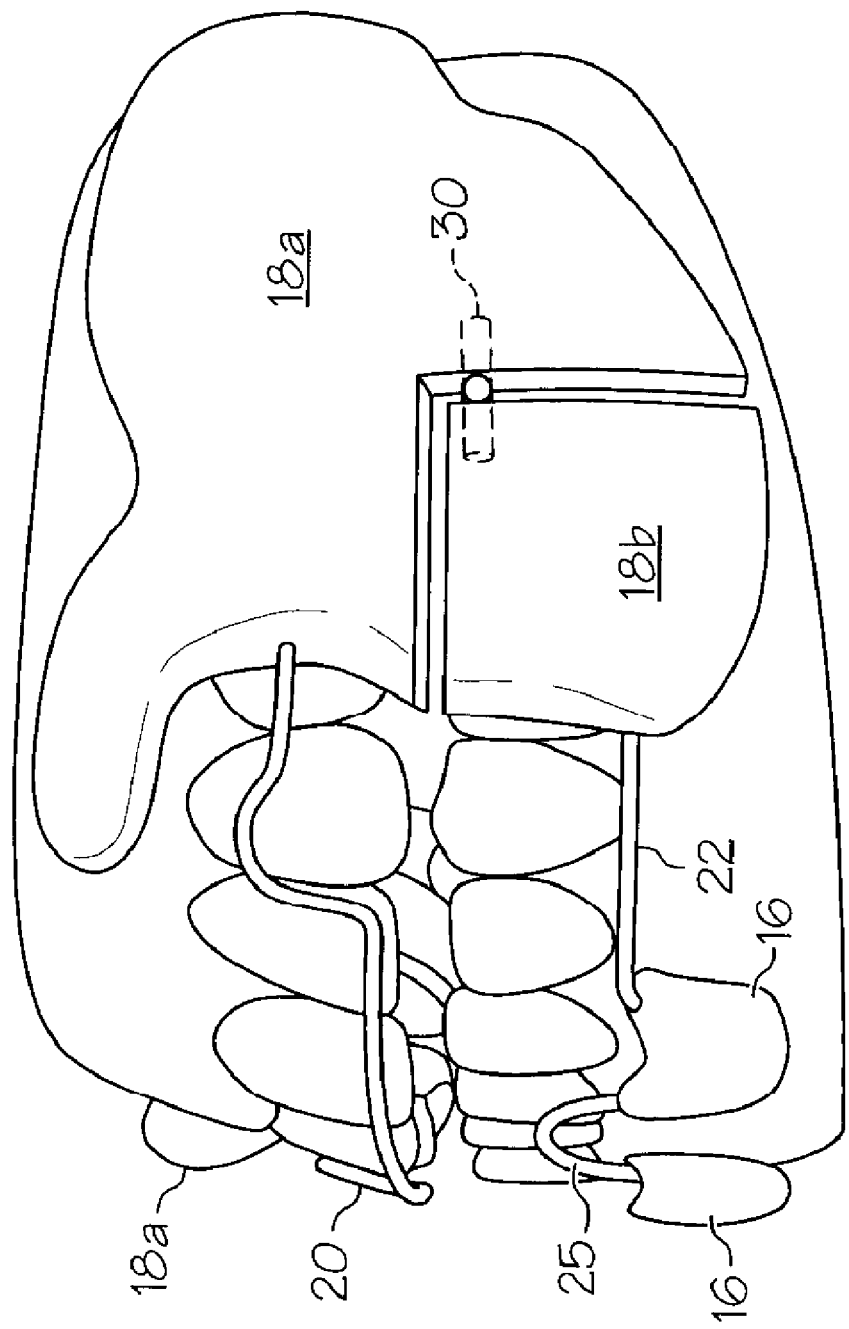
FIG. 4 is a side view of an embodiment of the apparatus of the invention in which bipartite buccal shields each include an expansion screw.

The lip pads 16, as best seen in FIGS. 2 and 4, sit between the gum and lower lip, act to support the mental-labial fold and alter the swallowing mechanism. The lip pads 16 engage the mental-labial fold, and act to interfere with and re-program the mentalis muscle inferiorly and support the mental-labial fold externally. In conjunction with the buccal shields 18, the lip pads 16 make it difficult to contract the mentalis muscle at the chin, and thereby cause the orbicularis oris muscle (a sphincter-type muscle around the mouth) and the buccinator muscles to raise the base of the tongue. The lip pads 16 also isolate and prevent the auxiliary muscles of the lip, especially but not exclusively the mentalis muscle, from contributing to the closure of the lip. The orbicularis oris muscle then must act as a sphincter which closes or seals the anterior part of the mouth. Compensations by other muscles in sealing the anterior part of the mouth for swallowing are no longer necessary, so the tongue can remain raised, and does not need to fall inferiorly and anteriorly to close the mouth and create an anterior seal. Altering the postural performance of this anterior muscle chain serves to alter the tongue's posture, all of the muscles of the face, the muscles of mastication, as well as the suprahyoid and infrahyoid muscles, to achieve a reduced resistance to air flow in the mouth and pharynx, and provide a new oral systemic balance which allows for better physiological function in breathing, speaking, chewing, and swallowing. Indeed, one of the goals of using the appliance of the present invention is to establish a new postural performance pattern for all of these muscles, so that a more beneficial physiological function of the upper airway can be obtained.

The buccal shields 18 engage the interior surfaces of the cheeks and serve to push the cheeks of the user laterally (outward) to increase the intraoral space and make more room within the lateral sides of the oral cavity, also known as the vestibule of the mouth, for the tongue and teeth. See FIGS. 2 and 4. The buccal shields 18 also work in conjunction with the lip pads 16 to alter the swallowing mechanism, as noted above, and prevent positive pressure from the atmosphere from sucking in the cheeks. In younger patients, the buccal shields 18 over time allow the jaw and teeth to develop in a lateral direction to their maximum capabilities.

FIG. 4 represents an alternative embodiment of the apparatus, in which an expansion screw 30 can be used to expand or shorten the size of the buccal shield. In this embodiment, each of the two buccal shields are divided into two pieces, 18a and 18b, yet connected by the expansion screw 30 so that their size can be altered. The expansion screws can be used to increase or decrease the distance between the two portions 18a and 18b of the buccal shield, and to bring the lower jaw forward, as shown in FIG. 4. By activating the screw 30, the portion 18b of the buccal shield moves anteriorly, as does the crossover wiring 24 with the lingual shield 12. This causes the lower jaw to be reflexly moved forward. Also, activation of the lingual nerve reflexly brings the tongue forward, as well as the lower jaw.

Polymers, plastics, rubbers, metals, and combinations thereof can be used to form the supports of the apparatus. For example, the supports can comprise a flexible and durable material, such as acrylic polymer. The dental wiring serves as reinforcement for the supports, and is intended to be moldable and bendable. Wiring is typically constructed of stainless steel metal wires having a diameter of between about 0.035 mm to about 1.20 mm, and preferably between about 0.035 mm to about 0.055 mm. The wiring provides form for the supports so they can function properly, as well as stabilize, strengthen and shape the apparatus. All of the wiring is typically stiff enough to maintain the acrylic supports in a stable formation, yet malleable enough for adjustment to fit each individual patient, so that the orthodontist can constantly reprogram the tongue and the muscles of the face and neck until airflow resistance is reduced in the mouth and pharynx and the proper oral systemic balance is achieved for each individual patient.

The appliance of the present invention is fabricated on a custom, per-patient basis. The components necessary for a preferred embodiment may be offered in "kit" form for fabrication of the appliances in local labs and offices. The preferred method of fabricating and custom-fitting the appliance to the patient comprises an initial office visit, lab work, and one or more follow-up visits before the apparatus is ready. Typically an X-ray of the patient's jaw and tongue posture, tonsils, adenoids, turbinates, soft palate and neck angle are taken to identify the hyoid bone and verify positioning. This positioning is later checked every several months by the orthodontist.

More specifically, the first office visit can include: 1) a sleep assessment—an Epworth sleepiness questionnaire is filled out by the patient and can be helpful in diagnosing sleep disorders. The Epworth sleepiness scale has been validated primarily in obstructive sleep apnea, and is used to measure excessive daytime sleepiness; 2) a medical history is obtained, including medication use (both prescription and natural); 3) an orthodontic record is created for the patient, including making mounted models of the mouth and teeth in order to create a personalized appliance for the patient; lateral, PA and panorex radiographs are typically taken; (potentially) an ICAT is done to determine baseline airway balance and any potential blockages; photographs are taken of the patient's face; the patient provides a history of their at-home sleeping, snoring and apneic events; and (potentially) a sleep study is scheduled at the sleep lab. The second office visit typically is a consultation to compile all patient records together. At the third visit the appliance (i.e. the apparatus of the present invention) is placed in order to begin treatment, specifically, titration of the patient's symptoms. During the 4$^{th}$ visit the side or buccal shields are adjusted and the lingual shields and lip pads are adjusted or activated for more effective improvements. Follow-up radiographs are taken at the 4$^{th}$ visit as well, and potentially a sleep study (either portable or at the sleep lab) is performed to ensure the final position of the apparatus and to maximize the potential for improvement of symptoms.

Lab procedures typically include creating the mounted models with plaster and wax; placing the wax in appropriate portions to ensure proper lip pad, buccal shield, palatal wafer and lingual shield position; bending the wiring to be used as struts and connections for the acrylic shields; placing of expansion screws for sequential advancement of the buccal shields; placing and curing liquid orthodontic acrylic on the wiring to unite and construct all plastic portions of the appliance; and processing the acrylic by boiling out the wax and then trimming and polishing the acrylic to its final size and shape.

The tissue-borne apparatus of the present invention has minimal tooth contact, thereby causing a more pronounced change in muscle patterns to establish the proper oral systemic balance between all muscle groups in the mouth, head and neck in order to open the airway. For children and teenagers, it also does not restrict any tooth movements that may be necessary for the process of exfoliation of the baby teeth, and allows for orthodontic tooth movement to allow the teeth to eventually (when treatment is completed) support the new jaw and tongue posture. The apparatus is typically inserted by the user after dinner and remains in place over night. Also, children users who are being treated for ADD (Attention Deficit Disorder) typically wear the apparatus 24 hours a day.

While the present invention has been illustrated by the description of embodiments and examples thereof, it is not intended to restrict or in any way limit the scope of the appended claims to such detail. Additional advantages and modifications will be readily apparent to those skilled in the art. Accordingly, departures may be made from such details without departing from the scope or spirit of the invention.

What is claimed is:

1. A removable, tissue-borne intraoral apparatus for relieving upper airway disorders, the apparatus comprising, in combination:
   a) supports comprising:
      i) a pair of lingual shields for engaging the inferior portion of the tongue and advancing the mandible, wherein the surfaces of the lingual shields engaged by the tongue are polished and concave and the edges are rounded, for directing the tongue to the upper surface of the lingual shields;
      ii) a palatal wafer for engaging the hard palate and controlling the tongue position, wherein the palatal wafer has a sloped configuration and allows the tongue to maintain contact with the anterior palatal ridge of the hard palate;
      iii) a pair of lip pads for engaging the mental-labial fold; and
      iv) a pair of buccal shields for engaging the interior surfaces of the cheeks; and
   b) reinforcement members anchored in the supports for interconnecting and reinforcing the supports, wherein wearing of the apparatus alters the position, configuration and freedom of movement of the tongue, the muscles of mastication, and the pharyngeal and facial muscles to reduce airflow resistance and alleviate upper airway disorders.

2. The apparatus of claim 1, the reinforcement members comprising:
   a) a labial wire for supporting the buccal shields, the labial wire including a first and a second vertical loop, wherein the first and second vertical loops can be expanded or contracted to alter the position of the buccal shields;

b) a mental wire for supporting the lip pads between the buccal shields, the mental wire including a third vertical loop that can be expanded or contracted to alter the position of the mental wire and the lip pads anteriorly or posteriorly;

c) a crossover wire for supporting the lingual shields between the buccal shields; and d) a palatal wire for supporting the palatal wafer between the buccal shields.

3. The apparatus of claim 1, further comprising a pair of upper molar stop wires, each molar stop wire projecting from the posterior portion of a corresponding buccal shield for creating a physical barrier to closing the upper and lower teeth together and preventing the appliance from rocking in the superior inferior direction, thereby improving airway patency and allowing more room for the tongue to move.

4. The apparatus of claim 1, wherein each of the buccal shields are divided into two pieces which can be adjusted via turning an expansion screw therein.

5. The apparatus of claim 1, wherein the supports arc made of acrylic.

6. The apparatus of claim 1, wherein the reinforcement members are stainless steel dental wires.

7. The apparatus of claim 1, wherein each reinforcement member has a thickness of between about 0.035 mm to about 1.20 mm.

8. A tissue-borne apparatus for relieving upper airway disorders, comprising, in combination:

a) a pair of lingual shields for engaging the tongue and advancing the mandible of a user, wherein the surfaces of the lingual shields engaged by the tongue are polished and concave and the edges are rounded, for directing the tongue to the upper surface of the lingual shields;

b) a palatal wafer for engaging the hard palate and controlling the anterior tongue position, wherein the palatal wafer has a sloped configuration and allows the tongue to maintain contact with the anterior palatal ridge of the hard palate;

c) a pair of lip pads for engaging the mental-labial fold;

d) a pair of buccal shields for engaging the interior surfaces of the cheeks and pushing the cheeks laterally; and e) a pair of upper molar stop wires for creating a physical barrier to closing the upper and lower teeth together and preventing the appliance from rocking in the superior inferior direction when in use, wherein each upper molar stop wire projects from the posterior portion of a corresponding buccal shield, wherein the lingual shields, palatal wafer, lip pads and buccal shields are connected to one another and reinforced by one or more reinforcement members, and wherein the apparatus alters the position, configuration and freedom of movement of the tongue, the muscles of mastication, and the pharyngeal and facial muscles to reduce resistance of air flow in the mouth and pharynx.

9. The apparatus of claim 8, the reinforcement members comprising:

a) a labial wire for supporting the buccal shields, the labial wire including a first and a second vertical loop, wherein the first and second vertical loops can be expanded or contracted to alter the position of the buccal shields;

b) a mental wire for supporting the lip pads between the buccal shields, the mental wire including a third vertical loop that can be expanded or contracted to alter the position of the mental wire and the lip pads anteriorly or posteriorly;

c) a crossover wire for supporting the lingual shields between the buccal shields; and d) a palatal wire for supporting the palatal wafer between the buccal shields.

10. The apparatus of claim 8, wherein each of the buccal shields are divided into two pieces which can be adjusted via turning an expansion screw therein.

11. The apparatus of claim 8, wherein the pair of lingual shields, the palatal wafer, the pair of lip pads and the pair of buccal shields are made of acrylic.

12. The apparatus of claim 8, wherein the reinforcement members are stainless steel dental wires.

13. The apparatus of claim 8, wherein each reinforcement member has a thickness of between about 0.035 mm to about 1.20 mm.

14. A method for re-orienting and reprogramming the muscles of the tongue and mouth in order to cause a decreased resistance to airflow in the mouth and pharynx, the method comprising the steps of:

a) providing supports for engaging the soft tissues of the mouth, the supports comprising a pair of lingual shields, a palatal wafer, a pair of lip pads, and a pair of buccal shields, wherein the lingual shields, palatal wafer, lip pads and buccal shields are connected to one another and reinforced by one or more reinforcement members; and b) arranging the supports and reinforcement members in the mouth of a user so that the lingual shields engage the inferior portion of the tongue and advance the mandible, the palatal wafer engages the hard palate and controls the anterior tongue position, the lip pads engage the mental-labial fold, and the buccal shields engage the interior surfaces of the cheeks, wherein the surfaces of the lingual shields engaged by the tongue are polished and concave and the edges are rounded, for directing the tongue to the upper surface of the lingual shields, wherein the palatal wafer has a sloped configuration and allows the tongue to maintain contact with the anterior palatal ridge of the hard palate, and wherein the supports and reinforcement members, used in combination, help the user achieve a reduced resistance to air flow in the mouth and pharynx and allows for better physiological function in breathing, speaking, chewing, and swallowing.

15. The method of claim 14, wherein each of the buccal shields are divided into two pieces which can be adjusted via turning an expansion screw therein.

* * * * *